United States Patent [19]

Nash

[11] Patent Number: 4,919,647
[45] Date of Patent: Apr. 24, 1990

[54] AORTICALLY LOCATED BLOOD PUMPING CATHETER AND METHOD OF USE

[75] Inventor: John Nash, Downingtown, Pa.

[73] Assignee: Kensey Nash Corporation, Exton, Pa.

[21] Appl. No.: 257,489

[22] Filed: Oct. 13, 1988

[51] Int. Cl.$^5$ .............................................. A61M 1/03
[52] U.S. Cl. ...................................... 600/16; 604/52; 604/151; 415/900
[58] Field of Search ................... 600/16; 604/52, 151; 128/303, 305; 27/24 A, 24 R; 415/126–128, DIG. 4

[56] References Cited

U.S. PATENT DOCUMENTS 4,625,712 12/1986 Wampler .
4,686,982 8/1987 Nash .................................... 128/305
4,688,998 8/1987 Olson et al. ........................... 604/16
4,753,221 6/1988 Kensey et al. .

Primary Examiner—Stephen C. Pellegrino
Attorney, Agent, or Firm—Caesar, Rivise, Bernstein, Cohen & Pokotilow, Ltd.

[57] ABSTRACT

A catheter and a method of use for pumping of blood through a living being's vascular system. The catheter has an expandable distal end portion and is introduced into the aorta so that that portion is at a predetermined position spaced from the aortic valve. The catheter comprises an expandable pump and a flexible, skirt-like barrier, both located at the distal end portion. The distal end portion also has an inlet and an outlet. When the catheter is located at the predetermined position its inlet is in fluid communication with the aorta distally of the pump while its outlet is in fluid communication with the aorta proximally of the pump, and the barrier engages the inner periphery of the aorta. Operating the pump causes blood to flow through the aorta, with the barrier ensuring that substantially all of the blood flows into the inlet to the pump means and out the outlet from the pump means and not around the exterior of the distal end portion of the catheter as the pump is operated.

22 Claims, 2 Drawing Sheets

AORTICALLY LOCATED BLOOD PUMPING CATHETER AND METHOD OF USE

This invention relates generally to medical instruments and more particularly to catheter based instruments for effecting the pumping of blood through the vascular system of a being and methods of using the same.

BACKGROUND OF THE INVENTION

Medical apparatus have been disclosed and are in use today to take over and/or to supplement the action of the heart to effect the pumping of blood into the vascular system. One particularly well known type of apparatus is the so-called "heart-lung" machine. Such prior art apparatus for effecting heart pumping action are necessarily complex and expensive. Most significantly such prior art devices are not suitable for general or widespread usage. In this connection, such prior art devices invariably require the services of skilled medical personnel, e.g., surgeons, under stringent surgical conditions for effecting the placement, connection and operation of the devices. Accordingly, various prior art blood pumping apparatus have not been deemed suitable for general or emergency usage to supplement or replace the pumping action of a person's heart.

In U.S. Pat. No. 4,625,712 (Wampler) there is disclosed a cardiac assist device in the form of a catheter having a small fixed size bladed pump at its distal end which is arranged to be passed by retrograde insertion through the aortic valve. The pump must necessarily be of a small size to enable the ready insertion of the catheter through the aortic valve. Thus, the device of the Wampler patent appears to be of limited blood pumping capacity.

In the U.S. Pat. No. 4,753,221, entitled Blood Pumping Catheter and Method of Use, of which I am a coinventor, and which is assigned to the same assignee as this invention, and whose disclosure is incorporated by reference herein, there is disclosed and claimed an instrument and a method of use which overcomes the disadvantages of the prior art, such as the Wampler patent.

To that end the instrument disclosed in my aforenoted patent is in the form of an elongated catheter having a distal end portion which is of sufficiently small diameter and sufficient flexibility to enable it to be passed through a portion of the being's vascular system so that the distal end portion of the catheter is located within or closely adjacent the being's heart. The catheter includes an expandable pump located at the distal end portion and drive means for effecting the operation of the pump. The distal end portion of the catheter includes an inlet for blood to flow therein and an outlet for blood to flow thereout. The instrument can be used for either left side heart applications or right side heart application. When used for left side heart applications, the catheter is constructed so that the inlet is in fluid communication with the left ventricle while the outlet is in fluid communication with the aorta. When used for right side heart applications, the catheter is constructed so that the inlet is in fluid communication with the right ventricle while the outlet is in fluid communication with the pulmonary artery. In one embodiment of that patent, the distal end portion of the instrument extended through the aortic valve. In another embodiment of that patent, the distal end portion is located over the aortic valve and includes a cover for that valve while enabling blood to flow therethrough. In all cases the blood can be pumped through the heart and into the vascular system without requiring any pumping action of the heart itself.

While the instrument and method of use disclosed in my foregoing patent is suitable for its intended use, the location of its distal end portion either through or over (i.e., immediately adjacent) the aortic valve limits the use of the device somewhat.

OBJECTS OF THE INVENTION

Accordingly, it is the general object of this invention to provide medical apparatus which overcomes the disadvantages of the prior art.

It is a further object of the instant invention to provide minimally invasive medical apparatus for taking over or supplementing the pumping action of the heart and which need not be located through or immediately adjacent the aortic valve.

It is a further object of this invention to provide minimally invasive catheter/pump apparatus which is simple in construction.

It is still a further object of this invention to provide a minimally invasive catheter/pump apparatus which readily locatable within the aorta at a location remote from the aortic valve and which is easy and safe to use.

SUMMARY OF THE INVENTION

These and other objects of the instant invention are achieved by providing a method and apparatus for pumping of blood through at least a portion of a living being's vascular system. The apparatus, in the form of an elongated catheter having a distal end portion, is introduced into the aorta so that the distal end portion is at a predetermined position in the aorta spaced away from the aortic valve. The catheter comprises pump means located at the distal end portion, barrier means located at the distal end portion, and drive means coupled to the pump means. The distal end portion of the apparatus comprises an inlet and an outlet. The apparatus is positioned so that the distal end portion is at the predetermined position with the inlet in fluid communication with the aorta distally of the pump means, the outlet in fluid communication with the aorta proximally of the pump means, and with the barrier means in engagement with the inner periphery of the aorta at the predetermined position. The pump means is operated by the drive means to pump the blood through the aorta. The barrier means ensures that substantially all of the blood flowing through the aorta flows into the inlet to the pump means and out the outlet from the pump means and not around the exterior of the distal end portion of the apparatus as the pump means is operated.

DESCRIPTION OF THE DRAWINGS

Other objects and many of the attendant advantages of this invention will be readily appreciated as the same becomes better understood by reference to the following detailed description when considered in connection with the accompanying drawings wherein.

DETAILED DESCRIPTION OF THE PREFERRED EMBODIMENT

Figure 1:
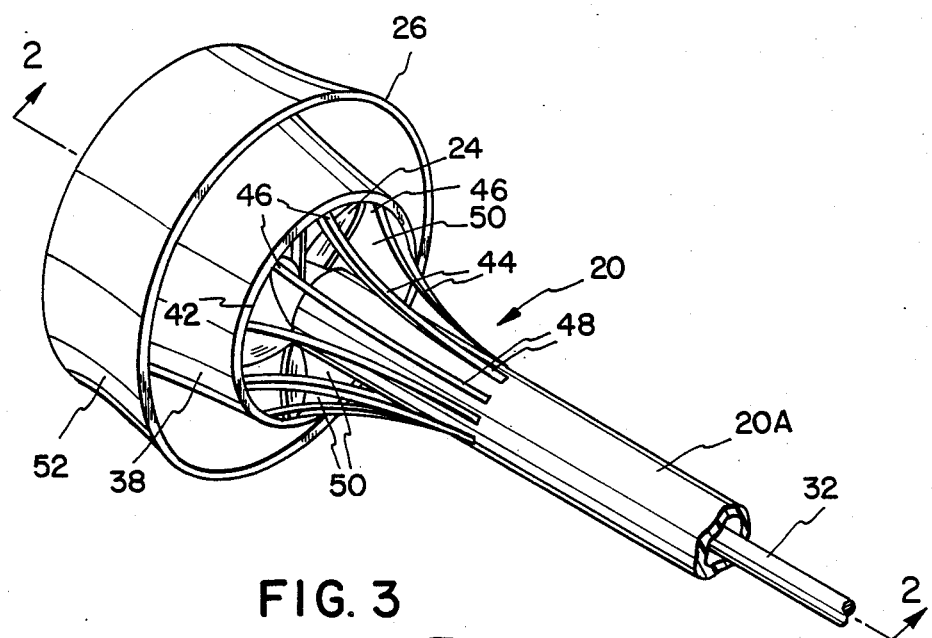
FIG. 1 is a perspective view of the distal end of the apparatus constructed in accordance with the subject invention.
Figure 2:
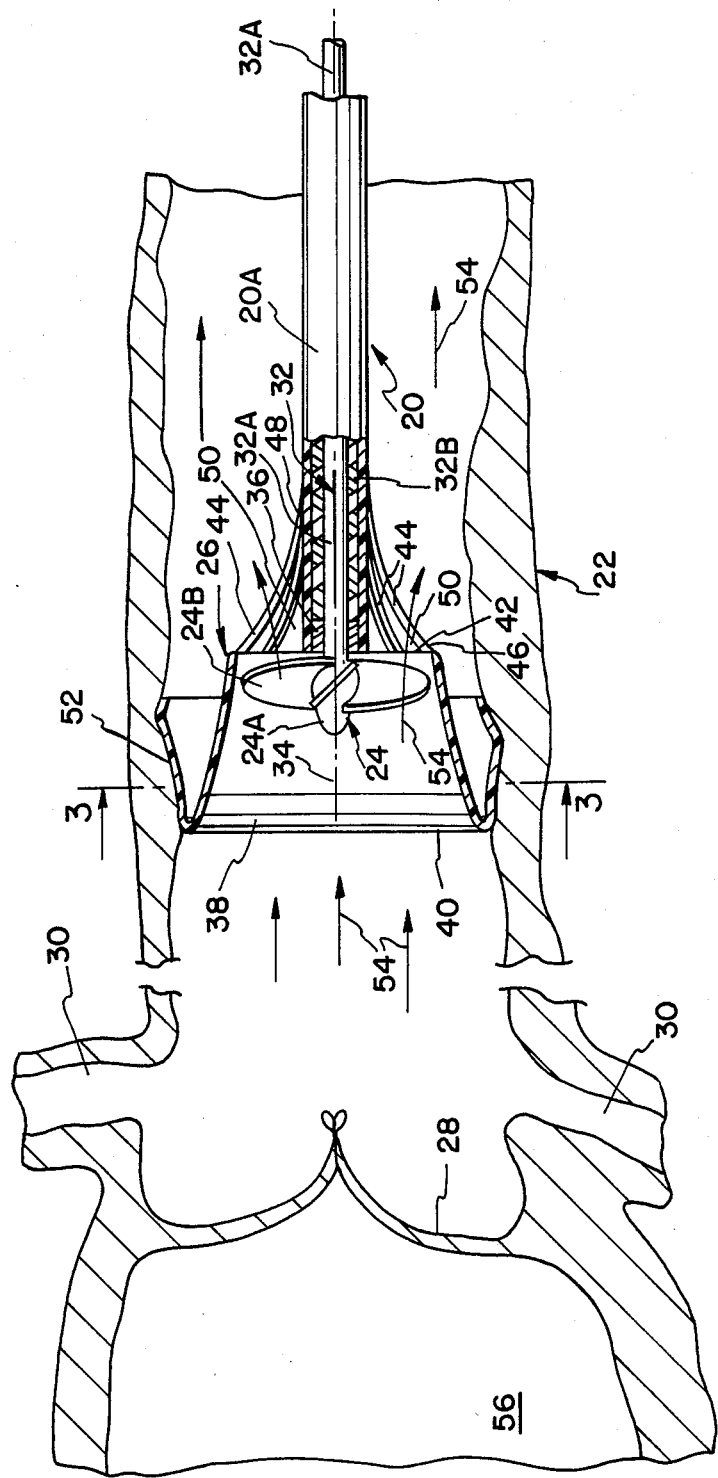
FIG. 2 is an enlarged sectional view taken along line 2—2 of FIG. 1 and showing the device of FIG. 1 in its operative state to pump blood to the being's vascular system.

Referring now in detail to the various figures of the drawing wherein like reference characters refer to like parts, there is shown at 20 in FIG. 1 apparatus constructed in accordance with the subject invention. That apparatus is arranged to be disposed within the vascular system, and in particular, the aorta 22 (FIG. 2) to effect the pumping of blood through the vascular system. Thus, the apparatus basically comprises a catheter having pumping means 24 located at its distal end portion 26. The details of the apparatus 20 will be described in detail later. Suffiee it for now to state that catheter comprises an elongated outer tube or jacket 20A of small diameter, e.g., 5 to 10 French (1.7-3.3 mm), with various components located therein and with the pumping means 24 and barrier means, to be described later at its distal end portion 26. The catheter is sufficiently flexible to enable it to be passed through the vascular system to its desired position within the aorta remote (i.e., downstream) from the aortic valve 28 (FIG. 2). The positioning of the catheter 20 is carried out through the use of a conventional tubular guide catheter (not shown), which is first introduced and threaded through the vascular system in a convention manner.

For example, the catheter 20 is inserted percutaneously into the femoral artery (not shown), up through the descending aorta (not shown) until its distal end portion 26 is located at a desired position within the aorta 22 downstream of the aortic valve 28 and downstream of the junction of the coronary arteries 30 to the aorta. Thus, the distal end portion 26 may be located within the ascending aorta, the aortic arch or the descending aorta, as desired.

As can be seen clearly in FIG. 2 the distal end portion 26 of the catheter 20 includes the heretofore identified pump means 24. That means can take various forms such as those disclosed in my aforenoted U.S. Pat. No. 4,753,221. Thus, the pump means 24 is preferably a centrifugal pump which is arranged to be operated, e.g., rotated, by drive means 32 shown. The drive means 32 can take various forms, but preferably comprises the high speed rotary drive system described and claimed in my U.S. Pat. No. 4,686,982 entitled Spiral Wire Bearing for Rotating Wire Drive Catheter, and in my copending U.S. patent application Ser. No. 938,698 filed on Dec. 5, 1986, entitled Catheter with Means to Prevent Wear Debris From Exiting, said patent and said application are both assigned to the same assignee as this invention, and the disclosures of both are incorporated by reference herein.

Basically that drive system comprises an elongated drive wire or cable 32A supported in the center of the catheter tube 20A, that is, along its central longitudinal axis 34, by means of a spiral bearing 32B. That bearing comprises a helical or spiral coil of wire extending substantially the entire length of the catheter tube from a proximately located point outside the body to the distal end portion of the catheter. The outer diameter of helical bearing is sufficiently great so that its loops just clear the interior surface of the catheter tube 20A to hold the bearing securely in place therein. The inside diameter of the central passage extending down the length of the helical bearing is just slightly greater than the outside diameter of the drive cable so the drive cable can rotate freely therein.

In the interests of reducing the size of any wear debris created by the rotation of the drive cable within the spiral bearing, the drive cable may be swaged or drawn to increase the engaging surface area thereof, while the crosssectional shape of the spiral bearing can be rectangular to also increase the engaging surface area, as disclosed in my aforenoted copending application.

The drive cable is arranged to be connected at the proximal end thereof to an electric motor (not shown) or some other drive means for rotating the cable at a high rate of speed, e.g., from 10,000 to 200,000 rpm, to effect the operation of the pump 24.

Figure 3:
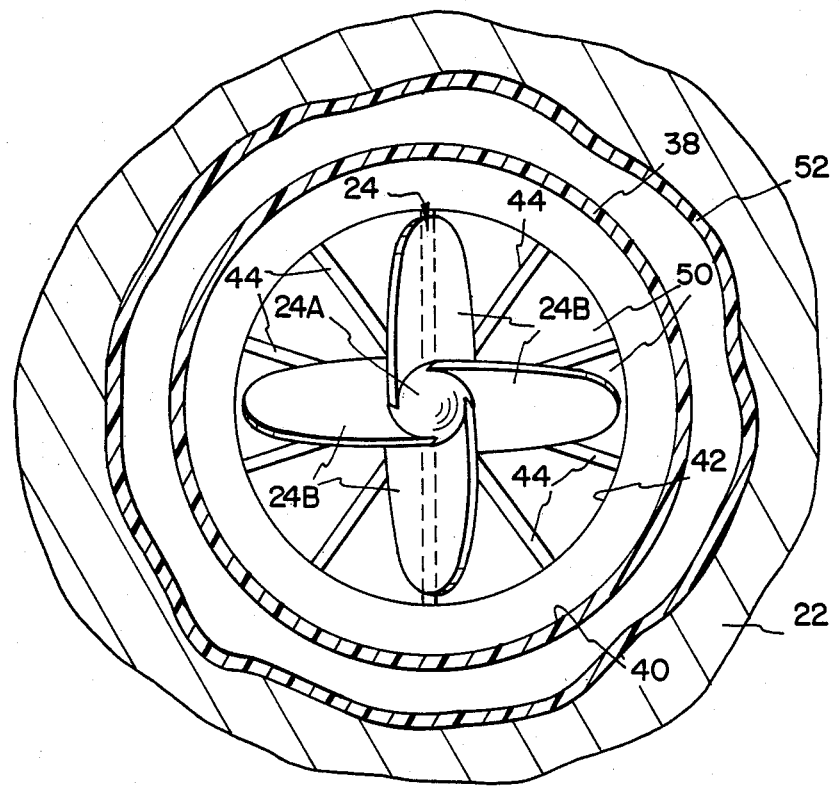
FIG. 3 is an enlarged sectional view taken along line 3—3 of FIG. 2.

The distal end portion of the catheter is of a generally tubular construction which is arranged to be expanded from a compacted orientation (not shown) to an expanded orientation (like that shown in FIGS. 1-3), and vice versa. When the distal end portion is in the compact orientation its outside diameter is sufficiently small to enable the catheter to be readily inserted longitudinally into the aorta, via a percutaneous insertion at a desired location, e.g., into the femoral artery. Once the catheter is within the aorta, and in particular at the desired position at which it is to be operated, the distal end portion is expanded to the expanded orientation shown in the drawing.

The pump 24 is an expandable/contractible member so that when the distal end portion of the catheter is expanded, automatically expands from a closed or compact position to the open, operative position.

In the embodiment shown herein, the pump 24 is an axial type pump basically comprising a central hub 24A from which four blades or impellers 24B extend. The blades are biased to naturally project outward radially. However, the blades are formed of flexible material so that when the distal end portion of the catheter 20 is compacted (unexpanded) the blades are flexed into the closed or compressed position extending beside one another. When released or freed they extend radially outward from the hub 24A. Moreover each of the blades 24B is angled so that when the pump is rotated about the central axis 34 of the catheter the blades 24B draw blood from the heart into an inlet (to be described later) in the distal end portion of the catheter to the blades and from there the blades force the blood out of an outlet in the direction of arrows (to be described later) into the aorta 22.

The proximal end of the hub 24A is connected to the distal end of the drive cable 32A so that the rotation of cable causes the concomitant rotation of pump's blades 24B.

The edges of each of the blades 24B are preferably rounded so as not to present any sharp edges which could adversely affect the blood cells pumped thereby.

The pump 24 is held in position centered within the device's distal end portion by a bearing support 36.

As can be seen the distal end portion of the catheter 20 is in the form of a cup-shaped member 38. The member 38 is formed of some other flexible and/or resilient material, e.g., an elastomeric material. The member 38 is tubular in shape, e.g., it constitutes a truncated cone, including an enlarged diameter open free end 40 located at the distal end thereof and a smaller diameter open end 42 located at the proximal end thereof. The cup-shaped member 38 is mounted on the sleeve 20A forming the outer wall of the catheter at the distal end thereof via a plurality of resilient fingers 44. The fingers extend at equally spaced locations about the periphery of the catheter's sleeve 20A. Each finger 44 is formed of a resilient material and is slightly arcuate in shape. The distal end 46 of each of the fingers 44 is fixedly secured to the outer periphery of the cup-shaped member immediately adjacent the opening 42 while the proximal end 48 of each of the fingers 44 is fixedly mounted to the catheter sleeve or tube 20A. Each of the fingers 44 is biased radially outward so that when unconstrained, they more to the expended position shown in the drawings, thereby expanding the cup-shaped member 38 from a compacted orientation (not shown), in which it is somewhat like a folded umbrella, to the expanded orientation shown. The fingers 44 and the cup-shaped member 38 are arranged to be compressed or contracted radially inward by being disposed within the tubular guide and/or introducing catheter (not shown) during placement of the device 20 in the patient. In particular, the device is arranged to be inserted through a conventional tubular guide/introducing catheter into the body to the desired position within the aorta and the guide/introducing catheter is then retracted to expose the distal end portion of device 20. This action enables the resilient fingers 44 to move radially outward to the position shown, thereby causing the cup-shaped member 38 to also assume the expanded orientation shown.

In normal operation the flared open end 40 of the cup-shaped member 38 serves as the inlet to the pump 24, while the smaller diameter opening 42 and the open spaces 50 between the fingers 44 contiguous with the opening 42 serves as the outlet from the pump. Thus the pump is located so that its blades are disposed within the cup shaped member 38 between the inlet and the outlet.

In order to ensure that substantial all, if not all, of the blood which will flow through the aorta flows into the pump's inlet (and not around the outside of the catheter), the distal end portion of the catheter includes the heretofore mentioned barrier means. That means is in the form of a barrier wall or a flexible skirt 62 which extends about the periphery of cup-shaped member 38 contiguous with the opening (inlet) 40. The skirt is very flexible so that it engages and conforms to the periphery of the inner surface of the aorta as shown clearly in FIGS. 2 and 3. This action has the effect of isolating the portion of the aorta 22 upstream (distally) of the pump from the portion of the aorta downstream (proximally) of the pump, except for the passageway through the pump itself, i.e., through the cup-shaped member 38 from the inlet to the outlet. Accordingly, when the pump is operated at a relatively high speed, e.g., 10,000–100,000 RPM, higher pressure is produced in the aorta downstream of the barrier wall than upstream. This action causes blood to be drawn in the direction of arrows 54 from the heart 56 through the aortic valve 28 into the pump's inlet 40, from whence it flows to the pump's outlet 42, 50 and from there into the aorta 22 for passage to the remainder of the person's vascular system.

In some applications, e.g., to ensure that sufficient blood flows into the coronary arteries 30, the operation of the catheter's pump will be coordinated with the pumping action of the heart. Thus, for such applications the speed of the pump is cycled, i.e., slowed down or stopped, in synchronism with the pumping action of the heart so that there will be repetitive periods when the higher pressure downstream of the pump pushes the blood upstream of the pump into the coronary arteries.

The pump speed/time cycle can be established and/or adjusted to anything desired.

Not only does the barrier wall 52 provide the isolation function described above, it also serves to hold the distal end of the catheter at the desired operative position within the aorta.

As will be appreciated from the foregoing since the catheter is arranged to be located at a position remote from the heart and the aortic valve, it can be used by less skilled personnel than would otherwise be required if the catheter had to be located into the heart through the aortic valve or immediately over the aortic valve. Moreover, some medical situations, e.g., a patient having a calcified aortic valve or whose heart has stopped beating, may not be conducive to the disposition of a catheter through or immediately over the aortic valve. It is for such applications that the subject catheter is particularly suited. Furthermore, the location of the distal end of the catheter remote from the aortic valve ensures that the entrance to the coronary arteries is not blocked by any portion of the catheter.

Without further elaboration, the forgoing will so fully illustrate my invention that others may, by applying current or future knowledge, readily adopt the same for use under various conditions of service.

What is claimed is:

1. Apparatus for disposition within the aorta of a living being to effect the pumping of blood through at least a portion of the being's vascular system, said apparatus comprising an elongated catheter having a distal end portion, said catheter being of sufficiently small diameter to enable it to be freely located within the aorta so that its distal end portion is at a predetermined position spaced away from and not in contact with the aortic valve, said apparatus comprising pump means located at said distal end portion, barrier means located at said distal end portion, and drive means coupled to said pump means for operating said pump means, whereupon blood is made to flow through said aorta, said distal end portion of said apparatus comprising an inlet in fluid communication with said aorta distally of said pump means and an outlet in fluid communication with said aorta proximally of said pump means, said barrier means comprising conformable wall means for closely engaging the inner periphery of said aorta at said predetermined position to ensure that substantially all of the blood flowing through the aorta flows into said inlet to said pump means and out said outlet from said pump means and not around the exterior of the distal end portion of said apparatus.

2. The apparatus of claim 1 wherein said wall means serves to hold the distal end portion of said apparatus in place at said predetermined position within said aorta.

3. The apparatus of claim 2 wherein said wall means comprises a flexible skirt extending about the periphery of said distal end portion.

4. The apparatus of claim 1 wherein said wall means comprises a flexible skirt extending about the periphery of said distal end portion.

5. The apparatus of claim 4 wherein said distal end portion of said apparatus comprises a tubular portion, said tubular portion including a first opening portion defining said inlet and an oppositely disposed second opening defining said outlet, said skirt extending about the periphery of said tubular portion between said first and second openings.

6. The apparatus of claim 5 wherein said wall means serves to hold the distal end portion of said apparatus in place at said predetermined position within said aorta.

7. The apparatus of claim 1 wherein said distal end portion of said apparatus comprises a tubular portion, said tubular portion including a first opening portion defining said inlet and an oppositely disposed second opening defining said outlet, said wall portion being located between said first and second openings.

8. The apparatus of claim 7 wherein said tubular portion is expandable from a compacted configuration to an expanded configuration and vice versa.

9. The apparatus of claim 8 wherein said wall portion comprises a flexible skirt extending about the periphery of said tubular portion.

10. The apparatus of claim 9 wherein said skirt is arranged to conform to the internal periphery of said aorta at said predetermined position.

11. The apparatus of claim 8 wherein said pump comprises at least one blade, said blade being movable from a compacted configuration to an expanded configuration.

12. Apparatus for disposition within the aorta of a living being to effect the pumping of blood through at least a portion of the being's vascular system, said apparatus comprising an elongated catheter having a distal end portion, said catheter being of sufficiently small diameter to enable it to be freely located within the aorta so that its distal end portion is at a predetermined position spaced away from the aortic valve, said apparatus comprising pump means located at said distal end portion, barrier means located at said distal end portion, and drive means coupled to said pump means for operating said pump means, whereupon blood is made to flow through said aorta, said distal end portion of said apparatus additionally comprising an inlet in fluid communication with said aorta distally of said pump means, an outlet in fluid communication with said aorta proximally of said pump means, and a tubular portion, said tubular portion comprising a first opening defining said inlet, an oppositely disposed second opening defining said outlet, a flexible sleeve and a plurality of elongated fingers disposed about the periphery of said distal end portion and supporting said sleeve, said fingers being arranged to be moved from a compacted position to an expanded position to expand said sleeve from a compacted configuration to an expanded configuration, said barrier means comprising a wall located between said first and second openings for engaging the inner periphery of said aorta at said predetermined position to ensure that substantially all of the blood flowing through the aorta flows into said inlet to said pump means and out said outlet from said pump means and not around the exterior of the distal end portion of said apparatus.

13. The apparatus of claim 12 wherein said sleeve comprises a pair of openings and wherein said outlet comprises spaces between said fingers and one end of said sleeve and wherein said inlet comprises the other opening of said sleeve.

14. Apparatus for disposition within the aorta of a living being to effect the pumping of blood through at least a portion of the being's vascular system, said apparatus comprising an elongated catheter having a distal end portion, said catheter being of sufficiently small diameter to enable it to be freely located within the aorta so that its distal end portion is at a predetermined position spaced away from the aortic valve, said apparatus comprising pump means located at said distal end portion, barrier means located at said distal end portion, and drive means coupled to said pump means for operating said pump means, whereupon blood is made to flow through said aorta, said distal end portion of said apparatus additionally comprising an inlet in fluid communication with said aorta distally of said pump means, an outlet in fluid communication with said aorta proximally of said pump means, and a tubular portion, said tubular portion comprising a flexible sleeve and a plurality of elongated fingers disposed about the periphery of said distal end portion and supporting said sleeve, said fingers being arranged to be moved from a compacted position to an expanded position to expand said sleeve from a compacted configuration to an expanded configuration, said pump comprising at least one blade, said blade being movable from a compacted configuration to an expanded configuration.

15. The apparatus of claim 14 wherein said sleeve comprises a pair of openings and wherein said outlet comprises spaces between said fingers and one end of said sleeve and wherein said inlet comprises the other opening of said sleeve.

16. A method for pumping of blood through at least a portion of a living being's vascular system, said method comprising introducing an elongated catheter having a distal end portion into the aorta with said distal end portion at a predetermined position spaced away from and not in contact with the aortic valve, said distal end portion comprising an inlet and an outlet, said catheter additionally comprising pump means located at said distal end portion, barrier means located at said distal end portion comprising conformable wall means, and drive means coupled to said pump means, said method comprising positioning said distal end portion of said catheter at said predetermined position so that said inlet is in fluid communication with said aorta distally of said pump means and said outlet is in fluid communication with said aorta proximally of said pump means, and with said conformable wall means in close engagement with the inner periphery of said aorta at said predetermined position, operating said pump means to pump said blood through said aorta, with said barrier means ensuring that substantially all of the blood flowing through the aorta flows into said inlet to said pump means and out said outlet from said pump means and not around the exterior of the distal end portion of said catheter as said pump means is operated.

17. The method of claim 16 additionally comprising the step of causing said distal end portion of said catheter to expand from a compacted configuration to an expanded configuration once said distal end portion is located within said aorta.

18. The method of claim 17 wherein said distal end portion of said catheter is held in said compacted configuration during the introduction of said catheter into the body of said being to enable it to be freely located at the predetermined position in the aorta, and once at said predetermined position said distal end portion is expanded to said expanded configuration.

19. The method of claim 18 wherein said pump comprises at least one movable blade which is moved from a compacted configuration to an expanded configuration once the distal end portion of said catheter is located at said predetermined position.

20. The method of claim 16 wherein the operation of the pump is controlled so the blood may flow into the coronary arteries of said being.

21. The method of claim 20 wherein the speed and/or duration of operation of said pump is controlled.

22. The method of claim 21 wherein the speed of said pump is reduced periodically in synchronism with the pumping action of the being's heart.

* * * * *